United States Patent [19]

Hussain et al.

[11] 4,242,330

[45] Dec. 30, 1980

[54] DERIVATIVE OF ASPIRIN

[75] Inventors: Anwar A. Hussain, Lexington, Ky.; James E. Truelove, Downington, Pa.; Harry B. Kostenbauder, Lexington, Ky.

[73] Assignee: The University of Kentucky Research Foundation, Lexington, Ky.

[21] Appl. No.: 43,814

[22] Filed: May 30, 1979

[51] Int. Cl.$^3$ .................... A61K 31/70; C07H 13/02
[52] U.S. Cl. .................... 424/180; 424/230; 424/235; 536/115; 536/119
[58] Field of Search .................... 424/180, 230, 235; 536/119, 115

[56] References Cited

U.S. PATENT DOCUMENTS

| | | | |
|---|---|---|---|
| 3,118,875 | 1/1964 | Adams, Jr. | 536/18 |
| 3,279,990 | 10/1966 | Rose et al. | 536/119 |
| 3,639,169 | 2/1972 | Broeg et al. | 424/230 |
| 3,764,668 | 10/1973 | Higuchi et al. | 424/230 |
| 3,887,700 | 6/1975 | Boncey et al. | 424/230 |
| 4,126,681 | 11/1978 | Reller | 424/235 |

FOREIGN PATENT DOCUMENTS

M1453  9/1962  France .

OTHER PUBLICATIONS

Turner, "Chem. Abst." vol. 58, pp. 11459–11460, 1963.

*Primary Examiner*—Johnnie R. Brown
*Attorney, Agent, or Firm*—Burns, Doane, Swecker & Mathis

[57] ABSTRACT

There is provided a novel derivative of 2-acetoxybenzoic acid, i.e., 1-O-(2'-acetoxy)benzoyl-α-D-2-deoxyglucopyranose, which is suitable for the attainment of high 2-acetoxybenzoic acid blood levels without irritation of the gastrointestinal lining.

12 Claims, No Drawings

DERIVATIVE OF ASPIRIN

BACKGROUND OF THE INVENTION

1. Field of the Invention

The present invention relates to 2-acetoxybenzoic acid and more particularly, the present invention relates to a therapeutically useful derivative of 2-acetoxybenzoic acid, i.e., 1-O-(2'-acetoxy)benzoyl-α-D-2-deoxyglucopyranose.

The novel compound of this invention exhibits analgesic, antipyretic, and antirheumatic therapeutic activity.

The compound, 2-acetoxybenzoic acid, is commonly known as "aspirin" and/or "acetylsalicylic acid", and is one of the most widely used compounds in the treatment of simple pain and inflammation. 2-Acetoxybenzoic acid is widely employed as an analgesic, an antipyretic, an anti-inflammatory and an antirheumatic agent, and it is particularly useful in the relief of fever, headache, myalgia, arthralgia and other pains associated with integumental structures. 2-Acetoxybenzoic acid is generally administered for these conditions in the form of a powder, particle, capsule, solution, tablet or other pharmaceutically acceptable dosage form because it is advantageous from the standpoint that chronic use of the compound will not lead to a tolerance of addiction thereof. Moreover, its toxicity is much lower than most compounds possessing similar pharmacologic activity. However, 2-acetoxybenzoic acid, as used for these purposes, is well-known by the practicing skilled artisan of the medical arts to exhibit certain unwanted and deliterious side effects. Specifically, it induces occult hemorrhaging in the gastrointestinal tract, which results from contact of the insoluble solid particulate of the compound with the gastrointestinal mucosa. As a result of this insolubilization, the very acidic particles of 2-acetoxybenzoic acid will adhere to the gastrointestinal mucosa in the form of crystals and such crystals, taken together with the acidic environment of the gastrointestinal lining, will produce microetching thereof, which in turn, leads to gastrointestinal bleeding.

2. Description of the Prior Art

To date, it is known that gastric bleeding can be diminished if (1) an aqueous solution of 2-acetoxybenzoic acid is administered, or (2) a buffered aqueous solution of 2-acetoxybenzoic acid is administered. However, such solutions leave much to be desired in that they are commercially and consumerwise unacceptable, i.e., water and/or buffered solutions are unacceptable as a suitable pharmaceutical dosage form.

One product on the market, commercially known as "Alka-Seltzer ®" is basically an alkaline effervescent 2-acetoxybenzoic acid formulation, which does exhibit satisfactory water solubility and dissolution, insofar as 2-acetoxybenzoic acid is concerned. However, at least three disadvantages are associated with this product. Firstly, the product is contained in a tablet form and must initially be dissolved in water prior to consumption. Secondly, because the product contains a high amount of sodium ion, it is unacceptable for administration to hypertensive patients (those who suffer from high blood pressure), because it has now been medically established that the sodium ion contributes to hypertension. Thirdly, the alkaline nature of the product per se alters the pH of the blood and urine to the alkaline side. Chronic use of this product could thus initiate alkalosis.

It has also been proposed to avoid the adverse effects of 2-acetoxybenzoic acid by the use of various esterified derivatives thereof, wherein transient blocking of the acidic carboxylic group of aspirin occurs. For instance, French Patent No. M1453 describes various antipyretic and analgesic compounds formed by esterifying 2-acetoxybenzoic acid with various sugars. Whether such derivatives are viable substitutes for 2-acetoxybenzoic acid depends not only upon whether these derivatives have therapeutic value per se, but to a larger extent upon whether these derivatives have the potential to revert to 2-acetoxybenzoic acid by hydrolysis in vivo.

In this regard, it is notable that certain derivatives of 2-acetoxybenzoic acid tend to hydrolyze so as to form the corresponding ester of salicylic acid and not aspirin. The following reaction scheme serves to illustrate the manner in which derivatives of 2-acetoxybenzoic acid may hydrolyze:

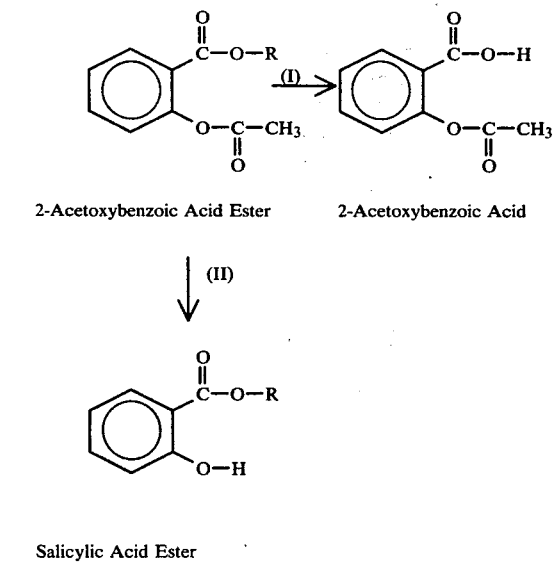

It is apparent that only those esterified derivatives of 2-acetoxybenzoic acid which hydrolyze according to reaction scheme (I), so as to produce aspirin, are viable substitutes for aspirin. Also, such a substitute must hydrolyze at a rate sufficient to release aspirin in therapeutically effective quantities.

It has recently been discovered that the aspirin derivative, 1-O-(2'-acetoxy)benzoyl-α-D-glucopyranose, tends to hydrolyze so as to form the corresponding sugar derivative of salicylic acid, as per reaction scheme (II) depicted above. Furthermore, to the extent that hydrolysis to aspirin takes place, such hydrolysis takes place only at a very slow rate.

In summary, the various prior art sugar derivatives of 2-acetoxybenzoic acid present a non-irritating neutral molecule to the gastrointestinal lining when administered for therapeutic purposes. However, the group which blocks the carboxylic acid function of 2-acetoxybenzoic acid tends to be bound thereto very tightly. Such prior art derivatives, therefore, do not release aspirin in vivo in therapeutically sufficient quantities. Thus, a need exists for a 2-acetoxybenzoic acid derivative, wherein transient blocking of the carboxylic function occurs, yet wherein the blocking group is not so tenaciously bound thereto.

SUMMARY OF THE INVENTION

Accordingly, it is one object of the present invention to provide a derivative of 2-acetoxybenzoic acid which does not tend to cause local irritation of the gastrointestinal tract, yet which is capable of hydrolyzing at a rate sufficient to release 2-acetoxybenzoic acid in vivo in therapeutically sufficient quantities.

It is another object of the present invention to provide a derivative of 2-acetoxybenzoic acid which will permit a therapeutically effective compound to be absorbed through the gastrointestinal lining, in a manner such that insoluble, acidic particles of 2-acetoxybenzoic acid are not contacted therewith, thus eliminating gastrointestinal bleeding.

Finally, it is yet another object of the present invention, to provide a derivative of 2-acetoxybenzoic acid, which can be formulated in a suitable oral pharmaceutically acceptable dosage form for administration as an analgesic, an antipyretic, an anti-inflammatory and an antirheumatic agent to warm-blooded animals.

These and other objects of the instant invention will become more readily apparent from a reading of the accompanying disclosure and appended claims thereto.

The foregoing objects are attained with the use of a novel acylal derivative of 2-acetoxybenzoic acid, i.e., 1-O-(2'-acetoxy)benzoyl-α-D-2-deoxyglucopyranose. The structure of this compound may be represented as follows:

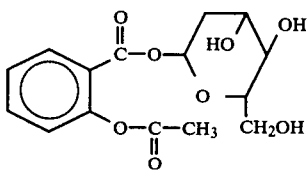

DETAILED DESCRIPTION OF THE INVENTION

1-O-(2'-acetoxy)benzoyl-α-D-2-deoxyglucopyranose can be synthesized according to the following scheme:

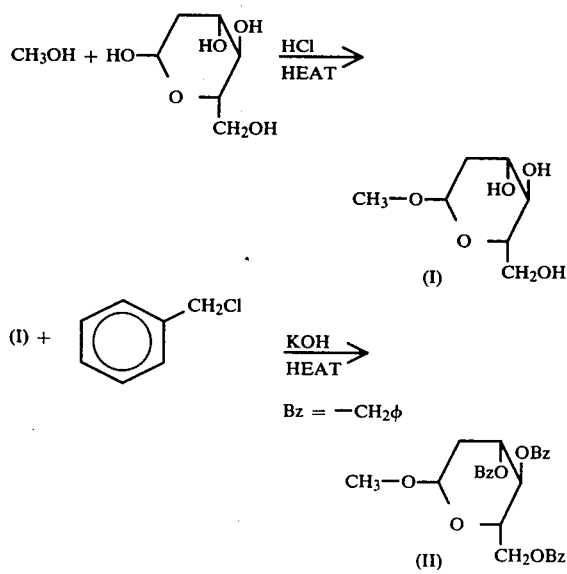

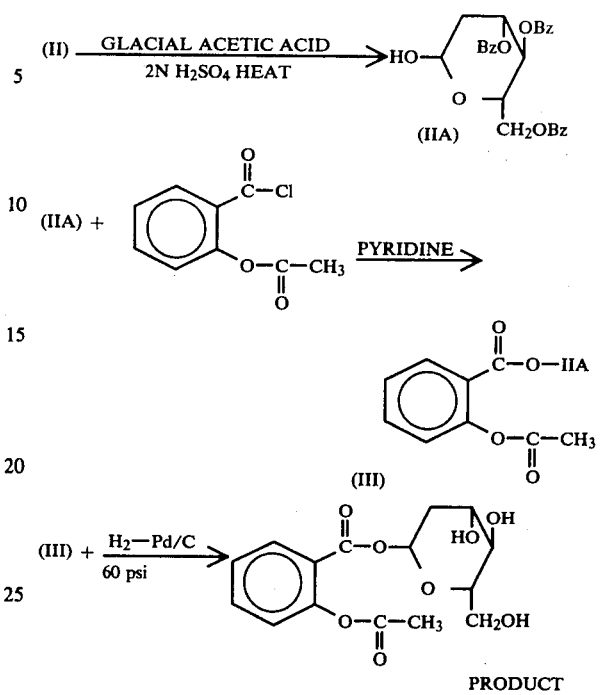

The above method is basically a modification of the method reported by Glaudemans and Fletcher in *Methods of Carbohydrate Chemistry*, Vol. VI, R. L. Whistler and J. N. Bemiller, Eds., Academic Press, New York, New York (1972), pp. 373–376.

Numerous modifications in the depicted reaction scheme will be apparent to those skilled in the art. For example, protecting groups other than benzyl can be employed, so long as they can be readily removed after coupling of the α-D-2-deoxyglucopyranose and 2-acetoxybenzoic acid portions of the molecule. Thus, p-methoxybenzyl or tert-butyl radicals could be introduced into the glucopyranose molecule instead of the benzyl protecting groups. After coupling, benzyl and p-methoxybenzyl protecting groups can be conveniently removed by catalytic hydrogenolysis. Suitable catalysts may include rhodium, platinum, ruthenium, Raney nickel and palladium (optionally on a support), a particularly preferred catalyst being palladium-on-carbon. When protecting groups which are normally not sensitive to catalytic hydrogenolysis, e.g., tert-butyl radicals, are employed, removal may be effected by use of an acid such as trifluoroacetic acid.

Variations in the coupling reaction would also be possible. For example, the acid chloride starting material could be reacted with the protected glucopyranose in the presence of suitable bases other than pyridine, e.g., other tertiary aliphatic or aromatic amines such as N-methylmorpholine, triethylamine, and picoline, conveniently in a non-protic solvent. Alternatively, the protected glucopyranose could be reacted with 2-acetoxybenzoic acid (rather than with the acid chloride), in which case the reaction would be conducted in the presence of a suitable dehydrating agent, for example, an aromatic or aliphatic carbodiimide.

The invention will appear more fully from the examples which follow.

EXAMPLE 1

Preparation of 1-O-methyl-α-D-2-deoxyglucopyranose

Fifteen grams (0.09 moles) of 2-deoxyglucose were dissolved in 540 milliliters of 2% methanolic hydrochloric acid and the solution was warmed to 40° C. in a water bath. The solution was shaken occasionally for one hour, then allowed to cool to room temperature and stirred with thirty-two grams of sodium carbonate for fifteen minutes. The solution was filtered and the filtrate was concentrated under diminished pressure to yield a light yellow oil containing a small amount of white solid. The oily mixture was then stirred vigorously with 750 milliliters of acetone for thirty minutes. The resulting suspension was filtered and the filtrate was concentrated under diminished pressure to yield a clear light yellow oil. The oil was combined with five milliliters of absolute ethanol and the mixture stored at −20° C. Large clear crystals of 1-O-methyl-α-D-2-deoxyglucopyranose separated spontaneously after two to three days. The crystalline material was recovered by filtration and washed with cold (−20° C.) ethyl acetate. NMR (DMSO-d$_6$): δ4.1–4.8(m,3,—O—H),δ3-.1–4.1(m,9,3–6 H's,1 H, —OC$\underline{H}_3$), δ1.1–2.3(m,2,2—H's).

EXAMPLE 2

Preparation of 1-O-methyl-3,4,6-tri-O-benzyl-α-D-2-deoxyglucopyranose

Nine grams (0.05 moles) of 1-O-methyl-α-D-2-deoxyglucopyranose was added to a suspension of 44.8 grams of finely powdered potassium hydroxide in 110 milliliters of dry dioxane and the mixture was warmed to reflux. When the reaction mixture was refluxing smoothly, sixty-two milliliters of colorless benzyl chloride was added dropwise over a period of about forty-five minutes. The mixture was refluxed for an additional period of forty minutes, then cooled. The apparatus was rearranged and the dioxane was distilled off over a period of three hours. The residue was cooled, diluted with water to a total volume of 350 milliliters, and extracted successively with 300, 200, 100 and 100 milliliter portions of ether. The ether portions were combined and dried over anhydrous sodium sulfate, then were filtered. Ether was removed from the filtrate under diminished pressure to yield a light yellow oil. The oily material was subjected to vacuum (10$^{-4}$ mm Hg) distillation with the bath temperature slowly increased to 200° C. The product, an amber-colored oil, remained in the distillation pot in 96–100% yield. NMR (CDCl$_3$); δ6.7–7.7(m,15,Ar$\underline{H}$), δ4.2–5.0(m,7,φ-C$\underline{H}_2$—O— and 1—H), δ3.4–4.2(m,5,3-through 6-glucose-H's), δ3.2(s,3,—OC$\underline{H}_3$), δ1.4–2.5 (m,2,2-position-H's).

EXAMPLE 3

Preparation of 3,4,6-tri-O-benzyl-α-D-2-deoxyglucopyranose

The amber oil obtained in Example 2 (22.3 grams, 0.05 moles) was dissolved in 550 milliliters of hot (70° C.) glacial acetic acid, 240 milliliters of hot (70° C.) molar sulfuric acid were slowly added, and the resulting mixture was maintained at 73°–75° C. for one hour. (The sulfuric acid was added slowly and with vigorous stirring to prevent precipitation of the starting material.) The reaction mixture was then slowly added to three liters of vigorously stirred water. The mixture was stirred for two hours, then was kept at +10° C. for twenty-four hours. Filtration and washing with two sixty-milliliter portions of methanol resulted in 14 grams (65% yield) of a white powder. Melting point: 96°–97° C. NMR (CDCl$_3$): δ6.7–7.7(m,15,Ar$\underline{H}$), δ5.1–5.4 (broad s,1,1—H), δ4.2–5.1(m,6,φ-C$\underline{H}_2$—O—), δ3.2–4.2(m,6,3-through 6-glucose-H's and 1-OH), δ1.4–2.5(m,2,2-position).

EXAMPLE 4

Preparation of 1-O-(2'-acetoxy)benzoyl-3,4,6-tri-O-benzyl-α-D-2-deoxyglucopyranose.

A solution of 13.7 grams (0.032 moles) of 3,4,6-tri-O-benzyl-α-D-2-deoxyglucopyranose in 130 milliliters of dichloromethane was treated with a solution of 6.93 grams (0.035 moles) o-acetylsalicyloyl chloride and 2.8 milliliters of dry pyridine in fifty milliliters of dichloromethane and the resulting mixture was stirred at room temperature. After twenty-three hours, 100 grams of ice were added and stirring was continued for one hour. The bi-layered mixture was transferred to a separatory funnel and the dichloromethane layer was washed successively with water, 3 N sulfuric acid, water, and a saturated aqueous solution of sodium bicarbonate. The dichloromethane layer was then dried over anhydrous sodium sulfate and filtered, and the filtrate was concentrated under diminished pressure to a clear oil in nearly quantitative yield. The oil, however, was found to contain varying amounts of a second component. This material was removed by dissolving the oily product in 200 milliliters of methanol at room temperature and then cooling the resultant solution to −20° C. The desired product was isolated as a waxy solid by decanting the methanol layer. This procedure was repeated with 50 milliliters of methanol, when necessary, to produce a unitary compound (TLC on silica gel with a mobile phase of chloroform/heptane/methanol/formic acid at 50/50/5/1, R$_f$0.57). The product was then isolated, in 25% yield, as white, crystalline flakes by recrystallization from absolute ethanol (twenty milliliters per gram of product). NMR (CDCl$_3$): δ6.7–8.0(m,19,Ar$\underline{H}$), δ5.8(d,1,1-H), δ4.4–4.9(m,6, —C$\underline{H}_2$—O—), δ3.4–3.9(m,5,3-through 6-position-H's), δ1.0–2.5(m,5,2-position and —OCOC$\underline{H}_3$).

EXAMPLE 5

Preparation of 1-O-(2'-acetoxy)benzoyl-α-D-2-deoxyglucopyranose

One gram of 1-O-(2'-acetoxy)benzoyl-3,4,6-tri-O-benzyl-α-D-2-deoxyglucopyranose was dissolved in 150 milliliters of absolute ethanol in a Parr bottle and 0.6 grams of 10% Pd/C was added. Hydrogenolysis at 60 pounds per square inch of hydrogen pressure was carried out for twelve hours. The reaction mixture was then filtered and the filtrate was concentrated under diminished pressure to a clear oil. The oil was washed with one fifty-milliliter portion of petroleum ether. The product crystallized spontaneously in 95–100% yields upon the addition of fifteen milliliters of chloroform. NMR(acetone-d$_6$): δ7.0–8.2(m,4,Ar$\underline{H}$), δ5.8–5.9(d,1,1-H), δ3.0–4.1(m8,3-through 6-H's and —OH's), δ2.3(s,3,—OCOC$\underline{H}_3$), δ1.0–2.3(m2,2-H's).

EXAMPLE 6

At low pH, the absorbance spectrum of 1-O-(2'-acetoxy)benzoyl-α-D-2-deoxyglucopyranose exhibits a large peak at 278 nanometers which is exactly like that observed for the unionized aspirin molecule. At a pH value of 6, the spectrum of the prodrug of the present invention remains unchanged, while that observed for the (ionized) aspirin molecule exhibits a significant decrease in absorbance at wavelengths of 270 to 290 nanometers. Therefore, the decrease in absorbance of a solution containing both the prodrug of this invention and aspirin observed at 285 nanometers upon adjustment of the pH to a value of six is proportional to the amount of aspirin in the solution.

Accordingly, the rate of generation of aspirin via hydrolysis of the derivative of the present invention was determined spectrophotometrically at 285 nm. Solutions of 1-O-(2'-acetoxy)benzoyl-α-D-2-deoxyglucopyranose in a buffered solution containing 5 mg/ml were freshly prepared and maintained at constant temperature in a circulating waterbath. An aliquot of 200 μl of the solution was added to 3 ml of buffered solution at pH 6 in a 1 cm path-length spectrophotometer cell (Cary cell), and, after inverting several times to insure a uniform mixture, the absorbance versus a buffer-only blank was observed at 285 nm. Buffers employed were hydrochloric acid (pH 1 to 2), citrate (pH 3), acetate (pH 4 to 6) and phosphate (pH 7-9). Ionic strength was adjusted with potassium chloride (usually to 0.1). The change in absorbance at 285 nm was followed until no change in absorbance was observed. First order plots were constructed by plotting log $(A_t - A_\infty)$ agains time. The effect of pH on the rate of hydrolysis was determined using solutions ranging from pH 1.2 to pH 9.

The generation of aspirin from the derivative was found to be independent of the pH of the solutions as shown in the Table. The half-life for the hydrolysis at pH 3 and pH 8 at 37° C. was found to be 7 minutes.

TABLE

THE HALF-LIFE OF HYDROLYSIS OF 1-O-(2'-ACETOXY)BENZOYL-α-D-2-DEOXYGLUCOPYRANOSE TO ASPIRIN AS A FUNCTION OF pH AT 37° C.

| pH | t1/2*(minutes) |
| --- | --- |
| 3 | 7 |
| 4.6 | 7.1 |
| 6.4 | 7.0 |
| 8 | 7.02 |
| 9 | 7.0 |

*Each half-life is the average of three determinations.

Thus, the transient blocking of the acidic carboxylic group of aspirin by formation of an acylal-linked derivative results in a compound which regenerates aspirin at an acceptable rate. Such a compound reduces the gastrointestinal liability of aspirin by presenting a neutral molecule to the gastric membrane.

EXAMPLE 7

The rate of hydrolysis of 1-O-(2'-acetoxy)benzoyl-α-D-glucopyranose, i.e., the compound of the formula

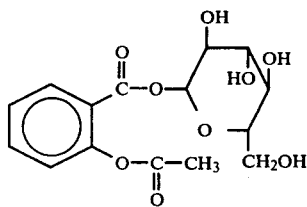

was determined by following the rate of appearance of aspirin in a solution by high pressure liquid chromatography. 1-O-(2'-acetoxy)benzoyl-α-D-glucopyranose was found to have a half-life of hydrolysis to aspirin of 55 hours.

The compound of this invention is conveniently administered in oral dosage form, such as by tablet or capsule, by combining the same in a therapeutic amount (e.g., dosage regimen for aspirin on an equivalent weight basis) with any oral pharmaceutically acceptable inert carrier, such as lactose, starch (pharmaceutical grade), dicalcium phosphate, calcium sulfate, kaolin, mannitol, and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethyleneglycol, ethylcellulose and waxes. Typical lubricants for use in these dosage forms can include, without limitation, sodium benzoate, sodium acetate, sodium chloride, leucine and polyethyleneglycol. Suitable disintegrators can include, without limitation, starch, methylcellulose, agar, bentonite, cellulose and wood products, alginic acid, guar gum, citrus pulp, carboxymethylcellulose and sodium lauryl sulfate. If desired, a conventionally pharmaceutically acceptable dye can be incorporated into the dosage unit form, i.e., any of the standard FD&C dyes.

Any skilled artisan can prepare these oral dosage forms by simply referring to the oral dosage form preparatory procedure outlined in "*REMINGTON'S PHARMACEUTICAL SCIENCES,*" Fourteenth Edition (1970), pp. 1659–1698, inclusive.

The dose administered, whether a single dose or a daily dose will, of course, vary with the needs of the individual being treated. However, the dosage administered is not subject to definite bounds, but it will usually be an effective therapeutic amount, or the equivalent on a molar basis of the pharmacologically-active form produced upon the metabolic release of the active drug (2-acetoxybenzoic acid) to achieve its desired pharmacological or physiological effect.

Although the present invention has been adequately described in the foregoing specification and examples included therein, it is apparent that various changes and/or modifications can be made thereto by the skilled artisan without departing from the spirit and scope thereof. Such changes and/or modifications are properly, equitably and intended to be within the full range of equivalence of the following claims.

What is claimed is:

1. The compound 1-O-(2'-acetoxy)benzoyl-α-D-2-deoxyglucopyranose.

2. A method for inducing an analgesic, antipyretic, antirheumatic or anti-inflammatory response in a warm-blooded animal which comprises orally administering thereto an effective amount of 1-O-(2'-acetoxy)benzoyl-α-D-2-deoxyglucopyranose.

3. A pharmaceutical composition of matter adapted for oral administration comprising an effective analgesic, antipyretic, antirheumatic or anti-inflammatory amount of 1-O-(2'-acetoxy)benzoyl-α-D-2-deoxyglucopyranose and a pharmaceutically acceptable inert carrier.

4. The method as defined by claim 2, for inducing an analgesic response.

5. The method as defined by claim 2, for inducing an antipyretic response.

6. The method as defined by claim 2, for inducing an antirheumatic response.

7. The method as defined by claim 2, for inducing an anti-inflammatory response.

8. The composition of claim 3, comprising an analgesic amount of said glucopyranose.

9. The composition of claim 3, comprising an antipyretic amount of said glucopyranose.

10. The composition of claim 3, comprising an antirheumatic amount of said glucopyranose.

11. The composition of claim 3, comprising an anti-inflammatory amount of said glucopyranose.

12. A compound having the structural formula:

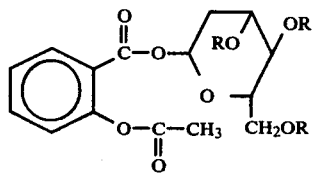

wherein R is selected from the group consisting of benzyl, p-methoxybenzyl and tert-butyl.